United States Patent
Lavrentovich et al.

(10) Patent No.: US 11,136,632 B2
(45) Date of Patent: Oct. 5, 2021

(54) COMMAND OF ACTIVE MATTER BY TOPOLOGICAL DEFECTS AND PATTERNS

(71) Applicant: Kent State University, Kent, OH (US)

(72) Inventors: Oleg D. Lavrentovich, Kent, OH (US); Chenhui Peng, Kent, OH (US); Taras Turiv, Kent, OH (US); Yubing Guo, Kent, OH (US); Qi-Huo Wei, Hudson, OH (US)

(73) Assignee: KENT STATE UNIVERSITY, Kent, OH (US)

( * ) Notice: Subject to any disclaimer, the term of this patent is extended or adjusted under 35 U.S.C. 154(b) by 173 days.

(21) Appl. No.: 16/100,394

(22) Filed: Aug. 10, 2018

(65) Prior Publication Data

US 2019/0048426 A1    Feb. 14, 2019

Related U.S. Application Data

(60) Provisional application No. 62/543,412, filed on Aug. 10, 2017.

(51) Int. Cl.

| | | |
|---|---|---|
| *C09K 19/54* | (2006.01) | |
| *C12R 1/125* | (2006.01) | |
| *C12R 1/07* | (2006.01) | |
| *C12R 1/08* | (2006.01) | |
| *C12R 1/12* | (2006.01) | |
| *C12R 1/09* | (2006.01) | |
| *C12R 1/10* | (2006.01) | |
| *C12R 1/11* | (2006.01) | |
| *C12R 1/085* | (2006.01) | |
| *C09K 19/52* | (2006.01) | |
| *C12N 1/20* | (2006.01) | |
| *C09K 19/56* | (2006.01) | |
| *C09K 19/60* | (2006.01) | |
| *C09K 19/04* | (2006.01) | |
| *C09K 19/20* | (2006.01) | |

(52) U.S. Cl.
CPC .............. *C12R 1/125* (2013.01); *C09K 19/52* (2013.01); *C09K 19/544* (2013.01); *C09K 19/56* (2013.01); *C09K 19/601* (2013.01); *C12N 1/20* (2013.01); *C12R 1/075* (2013.01); *C12R 1/08* (2013.01); *C12R 1/085* (2013.01); *C12R 1/09* (2013.01); *C12R 1/10* (2013.01); *C12R 1/11* (2013.01); *C12R 1/12* (2013.01); *C09K 2019/0448* (2013.01); *C09K 2019/2078* (2013.01)

(58) Field of Classification Search
CPC .................................................... C09K 19/601
See application file for complete search history.

(56) References Cited

PUBLICATIONS

Sivakumar et al., Adv. Funct. Mater., 2009, 19:2260-2265.*
Zhou et al., PNAS, 2014, 111(4):1265-1270.*
Ichimura, Chem. Rev., 2000, 100:1847-1873.*
Finnemeyer et al., J of Applied Physics, 2015, 118, (034501) pp. 1-8.*
Zhou et al., New J of Physics, 2017, 19, 055006, pp. 1-20.*

* cited by examiner

*Primary Examiner* — Bin Shen
(74) *Attorney, Agent, or Firm* — Fay Sharpe LLP

(57) ABSTRACT

A method for controlling self-propelled particles includes providing the particles to a liquid crystalline medium having predesigned local ordering. The method may control at least one of: a local concentration, trajectory, and net flow of self-propelled particles.

20 Claims, 1 Drawing Sheet

COMMAND OF ACTIVE MATTER BY TOPOLOGICAL DEFECTS AND PATTERNS

CROSS-REFERENCE TO RELATED APPLICATION

This application claims priority to U.S. Provisional Application No. 62/543,412, filed Aug. 10, 2017, which is incorporated herein by reference in its entirety.

STATEMENT CONCERNING FEDERALLY FUNDED RESEARCH

This invention was made with government support under Contract Nos. DMR-1507637, DMS-1434185, and CMMI-1436565 awarded by the National Science Foundation. The government has certain rights in the invention.

BACKGROUND

The present exemplary embodiment relates to systems, methods, and compositions for controlling active matter (e.g., self-propelled particles, either artificial such as colloidal particles or biological origin such as motile bacteria and sperm cells). It finds particular application in conjunction with methods for controlling motile bacteria, and will be described with particular reference thereto. However, it is to be appreciated that the present exemplary embodiment is also amenable to other like applications.

BRIEF DESCRIPTION

Self-propelled bacteria are marvels of nature with a potential to power dynamic materials and microsystems of the future. The challenge lies in commanding their chaotic behavior. By dispersing motile bacteria *Bacillus subtilis* in a liquid crystalline environment with spatially varying orientation of the anisotropy axis, distribution of bacterial concentration, as well as the geometry and polarity of their trajectories may be controlled. Bacteria recognize subtle differences in liquid crystal deformations, engaging in bipolar swimming in regions of pure splay and bend but switching to unipolar swimming in mixed splay-bend regions. They differentiate topological defects, heading toward defects of positive topological charge and avoiding negative charges, thus producing patterns of high and low concentrations that are determined by the preimposed pattern of liquid crystal orientation. Sensitivity of bacteria to preimposed orientational patterns represents a previously unknown facet of the interplay between hydrodynamics and topology of active matter.

Disclosed, in various embodiments, is a method for controlling at least one of the following features: a local concentration, trajectory, and net flow of self-propelled particles. The method includes: providing the self-propelled particles to a liquid crystalline medium having predesigned local ordering.

The self-propelled particles may be living or non-living (such as artificial colloidal particles). In some embodiments, the self-propelled particles are motile microorganisms, such as motile bacteria and/or sperm cells.

The motile bacteria may be of the genus *Escherichia*. In some embodiments, the bacteria species is *Escherichia coli*.

The motile bacteria may be of the genus *Bacillus*.

In some embodiments, the bacteria comprise at least one species selected from the group consisting of *Bacillus acidiceler, Bacillus acidicola, Bacillus acidiproducens, Bacillus acidocaldarius, Bacillus acidoterrestris. Bacillus aeolius, Bacillus aerius, Bacillus aerophilus, Bacillus agaradhaerens, Bacillus agri, Bacillus aidingensis, Bacillus akibai, Bacillus alcalophilus, Bacillus algicola, Bacillus alginolyticus, Bacillus alkalidiazotrophicus, Bacillus alkalinitrilicus, Bacillus alkalisediminis, Bacillus alkalitelluris, Bacillus altitudinis, Bacillus alveayuensis, Bacillus alvei, Bacillus amyloliquefaciens, Bacillus aminovorans, Bacillus amylolyticus, Bacillus andreesenii, Bacillus aneurinilyticus, Bacillus anthracis, Bacillus aquimaris, Bacillus arenosi, Bacillus arseniciselenatis, Bacillus arsenicus, Bacillus aurantiacus, Bacillus arvi, Bacillus aryabhattai, Bacillus asahii, Bacillus atrophaeus, Bacillus axarquiensis, Bacillus azotofixans, Bacillus azotoformans, Bacillus badius, Bacillus barbaricus, Bacillus bataviensis, Bacillus beijingensis, Bacillus benzoevorans, Bacillus beringensis, Bacillus berkeleyi, Bacillus beveridgei, Bacillus bogoriensis, Bacillus boroniphilus, Bacillus borstelensis, Bacillus brevis Migula, Bacillus butanolivorans, Bacillus canaveralius, Bacillus carboniphilus, Bacillus cecembensis, Bacillus cellulosilyticus, Bacillus centrosporus, Bacillus cereus, Bacillus chagannorensis, Bacillus chitinolyticus, Bacillus chondroitinus, Bacillus choshinensis, Bacillus chungangensis, Bacillus cibi, Bacillus circulans, Bacillus clarkia, Bacillus clausii, Bacillus coagulans, Bacillus coahuilensis, Bacillus cohnii, Bacillus composti, Bacillus curdlanolyticus, Bacillus cycloheptanicus, Bacillus cytotoxicus, Bacillus daliensis, Bacillus decisifrondis, Bacillus decolorationis, Bacillus deserti, Bacillus dipsosauri, Bacillus drentensis, Bacillus edaphicus, Bacillus ehimensis, Bacillus eiseniae, Bacillus enclensis, Bacillus endophyticus, Bacillus endoradicis, Bacillus farraginis, Bacillus fastidiosus, Bacillus fengqiuensis, Bacillus firmus, Bacillus flexus, Bacillus foraminis, Bacillus fordii, Bacillus formosus, Bacillus fortis, Bacillus fumarioli, Bacillus funiculus, Bacillus fusiformis, Bacillus galactophilus, Bacillus galactosidilyticus, Bacillus galliciensis, Bacillus gelatini, Bacillus gibsonii, Bacillus ginseng, Bacillus ginsengihumi, Bacillus ginsengisoli, Bacillus globisporus, Bacillus glucanolyticus, Bacillus gordonae, Bacillus gottheilii, Bacillus graminis, Bacillus halmapalus, Bacillus haloalkaliphilus, Bacillus halochares, Bacillus halodenitrificans, Bacillus halodurans, Bacillus halophilus, Bacillus halosaccharovorans, Bacillus hemicellulosilyticus, Bacillus hemicentroti, Bacillus herbersteinensis, Bacillus horikoshii, Bacillus horneckiae, Bacillus horti, Bacillus huizhouensis, Bacillus humi, Bacillus hwajinpoensis, Bacillus idriensis, Bacillus indicus, Bacillus infantis, Bacillus infernus, Bacillus insolitus, Bacillus invictae, Bacillus iranensis, Bacillus isabeliae, Bacillus isronensis, Bacillus jeotgali, Bacillus kaustophilus, Bacillus kobensis, Bacillus kochii, Bacillus kokeshiiformis, Bacillus koreensis, Bacillus korlensis, Bacillus kribbensis, Bacillus krulwichiae, Bacillus laevolacticus, Bacillus larvae, Bacillus laterosporus, Bacillus lautus, Bacillus lehensis, Bacillus lentimorbus, Bacillus lentus, Bacillus licheniformis, Bacillus ligniniphilus, Bacillus litoralis, Bacillus locisalis, Bacillus luciferensis, Bacillus luteolus, Bacillus luteus, Bacillus macauensis, Bacillus macerans, Bacillus macquariensis, Bacillus macyae, Bacillus malacitensis, Bacillus mannanilyticus, Bacillus marisflavi, Bacillus marismortui, Bacillus marmarensis, Bacillus massiliensis, Bacillus megaterium, Bacillus mesonae, Bacillus methanolicus, Bacillus methylotrophicus, Bacillus migulanus, Bacillus mirabilis, Bacillus mojavensis, Bacillus mucilaginosus, Bacillus muralis, Bacillus murimartini, Bacillus mycoides, Bacillus naganoensis, Bacillus nanhaiensis, Bacillus nanhaiisediminis, Bacillus nealsonii, Bacillus neidei, Bacillus neizhouensis, Bacillus niabensis,*

*Bacillus niacin, Bacillus novalis, Bacillus oceanisediminis, Bacillus odyssey, Bacillus okhensis, Bacillus okuhidensis, Bacillus oleronius, Bacillus oryzaecorticis, Bacillus oshimensis, Bacillus pabuli, Bacillus pakistanensis, Bacillus pallidus, Bacillus pallidus, Bacillus panacisoli, Bacillus panaciterrae, Bacillus pantothenticus, Bacillus parabrevis, Bacillus paraflexus, Bacillus pasteurii, Bacillus patagoniensis, Bacillus peoriae, Bacillus persepolensis, Bacillus persicus, Bacillus pervagus, Bacillus plakortidis, Bacillus pocheonensis, Bacillus polygoni, Bacillus polymyxa, Bacillus popilliae, Bacillus pseudalcalophilus, Bacillus pseudofirmus, Bacillus pseudomycoides, Bacillus psychrodurans, Bacillus psychrophilus, Bacillus psychrosaccharolyticus, Bacillus psychrotolerans, Bacillus pulvifaciens, Bacillus pumilus, Bacillus purgationiresistens, Bacillus pycnus, Bacillus qingdaonensis, Bacillus qingshengii, Bacillus reuszeri, Bacillus rhizosphaerae, Bacillus rigui, Bacillus ruris, Bacillus safensis, Bacillus salaries, Bacillus salexigens, Bacillus saliphilus, Bacillus schlegelii, Bacillus sediminis, Bacillus selenatarsenatis, Bacillus selenitireducens, Bacillus seohaeanensis, Bacillus shacheensis, Bacillus shackletonii, Bacillus siamensis, Bacillus silvestris, Bacillus simplex, Bacillus spiralis, Bacillus smithii, Bacillus soli, Bacillus solimangrovi, Bacillus solisalsi, Bacillus songklensis, Bacillus sonorensis, Bacillus sphaericus, Bacillus sporothermodurans, Bacillus stearothermophilus, Bacillus stratosphericus, Bacillus subterraneus, Bacillus subtilis, Bacillus taeanensis, Bacillus tequilensis, Bacillus thermantarcticus, Bacillus thermoaerophilus, Bacillus thermoamylovorans, Bacillus thermocatenulatus, Bacillus thermocloacae, Bacillus thermocopriae, Bacillus thermodenitrificans, Bacillus thermoglucosidasius, Bacillus thermolactis, Bacillus thermoleovorans, Bacillus thermophiles, Bacillus thermoruber, Bacillus thermosphaericus, Bacillus thiaminolyticus, Bacillus thioparans, Bacillus thuringiensis, Bacillus tianshenii, Bacillus trypoxylicola, Bacillus tusciae, Bacillus validus, Bacillus vallismortis, Bacillus vedderi, Bacillus velezensis, Bacillus vietnamensis, Bacillus vireti, Bacillus vulcani, Bacillus wakoensis, Bacillus weihenstephanensis, Bacillus xiamenensis, Bacillus xiaoxiensis,* and *Bacillus zhanjiangensis.*

The liquid crystalline medium may comprise a lyotropic chromonic liquid crystal confined between two plates.

In some embodiments, the plates are coated with a layer of photosensitive molecules.

The method may further include irradiating the photosensitive molecules with a light beam of linear polariziation that changes from point to point to thereby align the photosensitive molecules according to the local polarization; wherein the surface molecules align a director of liquid crystals in the liquid crystalline medium.

In some embodiments, the liquid crystalline medium comprises a liquid crystalline layer having a thickness of from about 2 μm to about 100 μm, including from about 3 μm to about 7 μm and from about 4.5 μm to about 5.5 μm.

The local ordering may include mixed splay-bend regions to create unipolar swimming; and/or pairs of semi-integer-strength or integer-strength defects to create a pumping action.

In some embodiments, the liquid crystalline medium comprises disodium chromoglycate dispersed in water.

Disclosed, in other embodiments, is a method for controlling motile bacteria comprising: providing a liquid crystal cell including a first plate, a first photoalignment layer, a liquid crystal layer comprising a lyotropic chromonic liquid crystal, a second photoalignment layer, and a second plate. The method further includes irradiating the first and second photoalignment layers to generate a spatially distorted pattern in each photoalignment layer; and providing the motile bacteria to the liquid crystal layer.

In some embodiments, the motile bacteria is *Bacillus subtilis*.

The lyotropic chromonic liquid crystal may be disodium chromoglycate dispersed in water.

In some embodiments, the liquid crystal layer has a thickness of about 5 μm.

The spatially distorted pattern may include at least one of: (A) arrays of periodically or non-periodically distorted director regions to control the concentration, trajectories and polarity of swimming bacteria, sperm cells, or self-propelled artificial particles; (B) arrays of periodically or non-periodically arranged topological defects of various strength or topological charge to control the concentration, trajectories and polarity of swimming bacteria, sperm cells, or self-propelled artificial particles; (C) mixed splay-bend regions to induce unipolar swimming; and (D) pairs of semi-integer-strength or integer-strength defects to induce a pumping action.

These and other non-limiting aspects of the present disclosure are more particularly described below.

DETAILED DESCRIPTION

Figure 1:
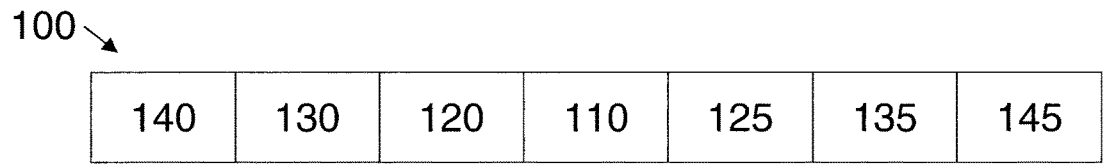
FIG. 1 is a schematic view of a non-limiting system in accordance with some embodiments of the present disclosure.

A more complete understanding of the systems, methods, and compositions disclosed herein can be obtained by reference to the accompanying drawings. These figures are merely schematic representations based on convenience and the ease of demonstrating the existing art and/or the present development, and are, therefore, not intended to indicate relative size and dimensions of the assemblies or components thereof.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent can be used in practice or testing of the present disclosure. The materials, methods, and articles disclosed herein are illustrative only and not intended to be limiting.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases that require the presence of the named ingredients/steps and permit the presence of other ingredients/steps. However, such description should be construed as also describing compositions, mixtures, or processes as "consisting of" and "consisting essentially of" the enumerated ingredients/steps, which allows the presence of only the named ingredients/steps, along with any impurities that might result therefrom, and excludes other ingredients/steps.

Unless indicated to the contrary, the numerical values in the specification should be understood to include numerical values which are the same when reduced to the same number of significant figures and numerical values which differ from the stated value by less than the experimental error of the conventional measurement technique of the type used to determine the particular value.

All ranges disclosed herein are inclusive of the recited endpoint and independently combinable (for example, the range of "from 2 to 10" is inclusive of the endpoints, 2 and 10, and all the intermediate values). The endpoints of the ranges and any values disclosed herein are not limited to the precise range or value; they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. The modifier "about" should also be considered as disclosing the range defined by the absolute values of the two endpoints. For example, the expression "from about 2 to about 4" also discloses the range "from 2 to 4."

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The present disclosure relates to systems and methods for controlling active matter using topological defects and patterns.

FIG. 1 schematically illustrates a liquid crystal cell 100 which may be used in accordance with some of the systems and methods of the present disclosure. The cell 100 includes a liquid crystal layer 110 sandwiched between a first plate 140 and a second plate 145. A first photoalignment layer 130 has been deposited on the first plate 140 and a second photoalignment layer 135 has been deposited on the second plate 145. A first alignment layer 120 resides between the first photoalignment layer 130 and the liquid crystal layer 110. A second photoalignment layer 125 resides between the second photoalignment layer 135 and the liquid crystal layer 110.

The liquid crystal layer 110 may have a thickness of from about 3 µm to about 7 µm, including from about 4.5 µm to about 5.5 µm, or about 5 µm.

The liquid crystal layer 110 contains a liquid crystal (e.g., a lyotropic chromonic liquid crystal) which may be dispersed/dissolved in a suitable solvent.

Irradiation of the photoalignment layers 130, 135 may be performed to generate a spatially-distorted pattern.

The first and second plates 140, 145 may be transparent. In some embodiments, the first and second plates 140, 145 are made of glass.

Figure 2:
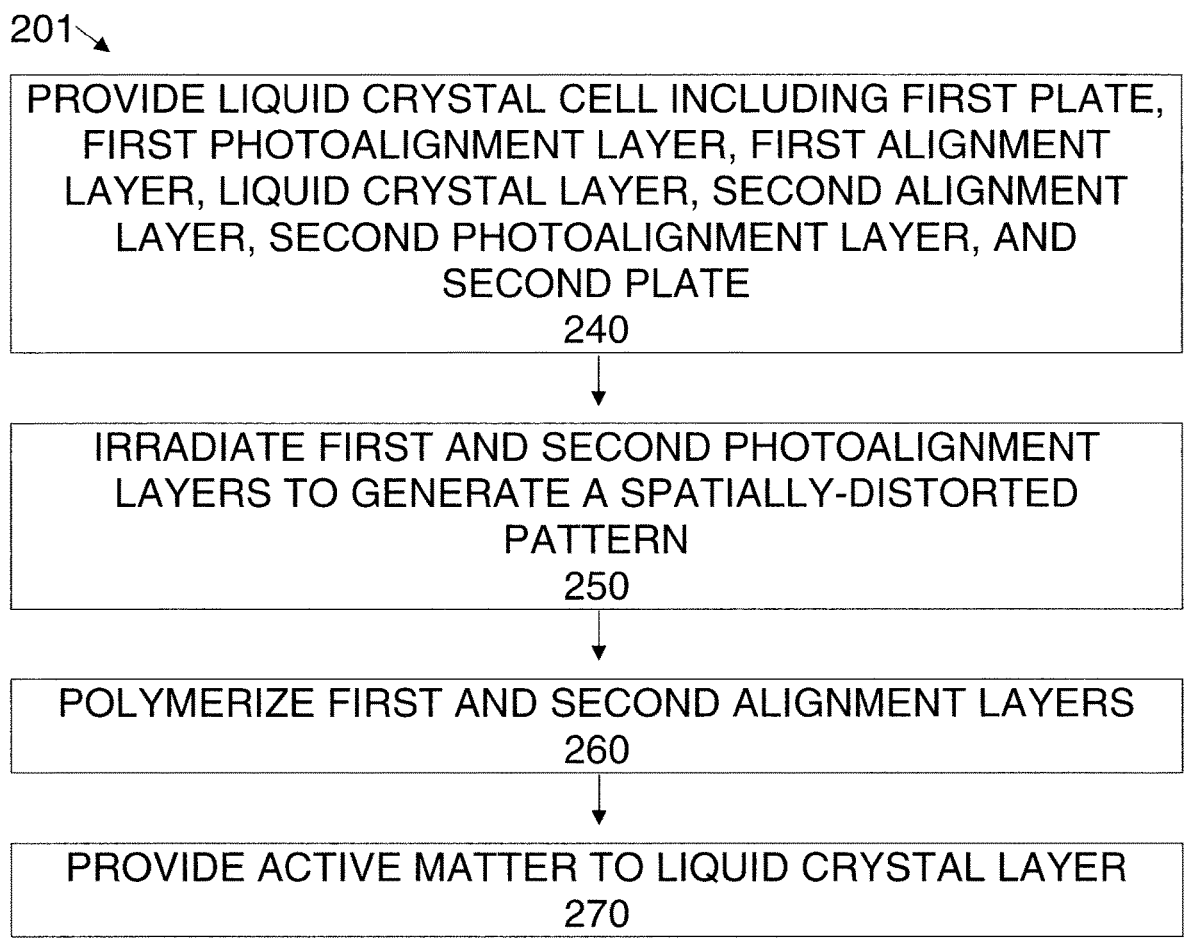
FIG. 2 is a flow chart of a non-limiting method in accordance with some embodiments of the present disclosure.

FIG. 2 is a flow chart showing a method 201 which may be used in accordance with some embodiments of the present disclosure. The method 201 includes providing a liquid crystal cell 240. The liquid crystal cell includes a first plate, a first photoalignment layer, a second alignment layer, a liquid crystal layer, a third alignment layer, a fourth photoalignment layer, and a second plate. The method 201 further includes irradiating the photoalignment layers to generate a spatially-distorted pattern 250. The method 201 further includes polymerization of alignment layers 260.

The method 201 also includes providing active matter to the liquid crystal layer 270. Although photoalignment is disclosed in some embodiments, other patterning techniques may be used as an alternative or in addition to photopatterning.

The active matter may be living or non-living. In some embodiments, the active matter includes self-propelling particles such as Janus spheres and Janus rods and motile biological organisms such as bacteria and sperm cells.

In some embodiments, the self-propelling particles are self-propelling microorganisms such as motile bacteria.

In some embodiments, the bacteria are Cocci bacteria. Cocci bacteria are round, oval, or spherical in shape. The Cocci bacteria may be arranged in the following configurations: diplococci, streptococci, tetrad, sarcinae, and staphylococci.

In some embodiments, the bacteria are Bacilli bacteria. Bacili bacteria are rod-shaped cells with flagellae appendages which propel the bacterium. The Bacili bacteria may be arranged in the following configurations: monobacillus, diplobacili, streptobacilli, palisades, and coccobacillus.

In some embodiments, the bacteria are Spirilla bacteria. Spirilla bacteria are twisted and commonly found in the form of spirillum and spirochetes.

The mobile bacteria may be selected from the *Bacillus* genus, the *Vibrio* genus, *Selenomonas*, and/or the *Listeria* genus. In particular embodiments, the bacteria is *Escherichia coli*.

The bacteria from the *Bacillus* genus may include one or more of the following: *Bacillus acidiceler, Bacillus acidicola, Bacillus acidiproducens, Bacillus acidocaldarius, Bacillus acidoterrestris. Bacillus aeolius, Bacillus aerius, Bacillus aerophilus, Bacillus agaradhaerens, Bacillus agri, Bacillus aidingensis, Bacillus akibai, Bacillus alcalophilus, Bacillus algicola, Bacillus alginolyticus, Bacillus alkalidiazotrophicus, Bacillus alkalinitrilicus, Bacillus alkalisediminis, Bacillus alkalitelluris, Bacillus altitudinis, Bacillus alveayuensis, Bacillus alvei, Bacillus amyloliquefaciens, Bacillus aminovorans, Bacillus amylolyticus, Bacillus andreesenii, Bacillus aneurinilyticus, Bacillus anthracis, Bacillus aquimaris, Bacillus arenosi, Bacillus arseniciselenatis, Bacillus arsenicus, Bacillus aurantiacus, Bacillus arvi, Bacillus aryabhattai, Bacillus asahii, Bacillus atrophaeus, Bacillus axarquiensis, Bacillus azotofixans, Bacillus azotoformans, Bacillus badius, Bacillus barbaricus, Bacillus bataviensis, Bacillus beijingensis, Bacillus benzoevorans, Bacillus beringensis, Bacillus berkeleyi, Bacillus beveridgei, Bacillus bogoriensis, Bacillus boroniphilus, Bacillus borstelensis, Bacillus brevis Migula, Bacillus butanolivorans, Bacillus canaveralius, Bacillus carboniphilus, Bacillus cecembensis, Bacillus cellulosilyticus, Bacillus centrosporus, Bacillus cereus, Bacillus chagannorensis, Bacillus chitinolyticus, Bacillus chondroitinus, Bacillus choshinensis, Bacillus chungangensis, Bacillus cibi, Bacillus circulans, Bacillus clarkia, Bacillus clausii, Bacillus coagulans, Bacillus coahuilensis, Bacillus cohnii, Bacillus composti, Bacillus curdlanolyticus, Bacillus cycloheptanicus, Bacillus cytotoxicus, Bacillus daliensis, Bacillus decisifrondis, Bacillus decolorationis, Bacillus deserti, Bacillus dipsosauri, Bacillus drentensis, Bacillus edaphicus, Bacillus ehimensis, Bacillus eiseniae, Bacillus enclensis, Bacillus endophyticus, Bacillus endoradicis, Bacillus farraginis, Bacillus fastidiosus, Bacillus fengqiuensis, Bacillus firmus, Bacillus flexus, Bacillus foraminis, Bacillus fordii, Bacillus formosus, Bacillus fortis, Bacillus fumarioli, Bacillus funiculus, Bacillus fusiformis, Bacillus galactophilus, Bacillus galactosidilyticus, Bacillus galliciensis, Bacillus* gelatini, Bacillus gibsonii, Bacillus ginseng, Bacillus ginsengihumi, Bacillus ginsengisoli, Bacillus globisporus, Bacillus glucanolyticus, Bacillus gordonae, Bacillus gottheilii, Bacillus graminis, Bacillus halmapalus, Bacillus haloalkaliphilus, Bacillus halochares, Bacillus halodenitrificans, Bacillus halodurans, Bacillus halophilus, Bacillus halosaccharovorans, Bacillus hemicellulosilyticus, Bacillus hemicentroti, Bacillus herbersteinensis, Bacillus horikoshii, Bacillus horneckiae, Bacillus horti, Bacillus huizhouensis, Bacillus humi, Bacillus hwajinpoensis, Bacillus idriensis, Bacillus indicus, Bacillus infantis, Bacillus infernus, Bacillus insolitus, Bacillus invictae, Bacillus iranensis, Bacillus isabeliae, Bacillus isronensis, Bacillus jeotgali, Bacillus kaustophilus, Bacillus kobensis, Bacillus kochii, Bacillus kokeshiiformis, Bacillus koreensis, Bacillus korlensis, Bacillus kribbensis, Bacillus krulwichiae, Bacillus laevolacticus, Bacillus larvae, Bacillus laterosporus, Bacillus lautus, Bacillus lehensis, Bacillus lentimorbus, Bacillus lentus, Bacillus licheniformis, Bacillus ligniniphilus, Bacillus litoralis, Bacillus locisalis, Bacillus luciferensis, Bacillus luteolus, Bacillus luteus, Bacillus macauensis, Bacillus macerans, Bacillus macquariensis, Bacillus macyae, Bacillus malacitensis, Bacillus mannanilyticus, Bacillus marisflavi, Bacillus marismortui, Bacillus marmarensis, Bacillus massiliensis, Bacillus megaterium, Bacillus mesonae, Bacillus methanolicus, Bacillus methylotrophicus, Bacillus migulanus, Bacillus mirabilis, Bacillus mojavensis, Bacillus mucilaginosus, Bacillus muralis, Bacillus murimartini, Bacillus mycoides, Bacillus naganoensis, Bacillus nanhaiensis, Bacillus nanhaiisediminis, Bacillus nealsonii, Bacillus neidei, Bacillus neizhouensis, Bacillus niabensis, Bacillus niacin, Bacillus novalis, Bacillus oceanisediminis, Bacillus odyssey, Bacillus okhensis, Bacillus okuhidensis, Bacillus oleronius, Bacillus oryzaecorticis, Bacillus oshimensis, Bacillus pabuli, Bacillus pakistanensis, Bacillus pallidus, Bacillus pallidus, Bacillus panacisoli, Bacillus panaciterrae, Bacillus pantothenticus, Bacillus parabrevis, Bacillus paraflexus, Bacillus pasteurii, Bacillus patagoniensis, Bacillus peoriae, Bacillus persepolensis, Bacillus persicus, Bacillus pervagus, Bacillus plakortidis, Bacillus pocheonensis, Bacillus polygoni, Bacillus polymyxa, Bacillus popilliae, Bacillus pseudalcalophilus, Bacillus pseudofirmus, Bacillus pseudomycoides, Bacillus psychrodurans, Bacillus psychrophilus, Bacillus psychrosaccharolyticus, Bacillus psychrotolerans, Bacillus pulvifaciens, Bacillus pumilus, Bacillus purgationiresistens, Bacillus pycnus, Bacillus qingdaonensis, Bacillus qingshengii, Bacillus reuszeri, Bacillus rhizosphaerae, Bacillus rigui, Bacillus minis, Bacillus safensis, Bacillus salaries, Bacillus salexigens, Bacillus saliphilus, Bacillus schlegelii, Bacillus sediminis, Bacillus selenatarsenatis, Bacillus selenitireducens, Bacillus seohaeanensis, Bacillus shacheensis, Bacillus shackletonii, Bacillus siamensis, Bacillus silvestris, Bacillus simplex, Bacillus spiralis, Bacillus smithii, Bacillus soli, Bacillus solimangrovi, Bacillus solisalsi, Bacillus songklensis, Bacillus sonorensis, Bacillus sphaericus, Bacillus sporothermodurans, Bacillus stearothermophilus, Bacillus stratosphericus, Bacillus subterraneus, Bacillus subtilis, Bacillus taeanensis, Bacillus tequilensis, Bacillus thermantarcticus, Bacillus thermoaerophilus, Bacillus thermoamylovorans, Bacillus thermocatenulatus, Bacillus thermocloacae, Bacillus thermocopriae, Bacillus thermodenitrificans, Bacillus thermoglucosidasius, Bacillus thermolactis, Bacillus thermoleovorans, Bacillus thermophiles, Bacillus thermoruber, Bacillus thermosphaericus, Bacillus thiaminolyticus, Bacillus thioparans, Bacillus thuringiensis, Bacillus tianshenii, Bacillus trypoxylicola, Bacillus tusciae, Bacillus validus, Bacillus vallismortis, Bacillus vedderi, Bacillus velezensis, Bacillus vietnamensis, Bacillus vireti, Bacillus vulcani, Bacillus wakoensis, Bacillus weihenstephanensis, Bacillus xiamenensis, Bacillus xiaoxiensis, and Bacillus zhanjiangensis.

The bacteria from the Listeria genus may include one or more of the following: Listeria aquatic, Listeria booriae, Listeria cornellensis, Listeria fleischmannii, Listeria floridensis, Listeria grandensis, Listeria grayi, Listeria innocua, Listeria ivanovii, Listeria marthii, Listeria monocytogenes, Listeria newyorkensis, Listeria riparia, Listeria rocourtiae, Listeria seeligeri, Listeria weihenstephanensis, and Listeria welshimeri.

The bacteria from the Vibrio genus may include one or more of the following: Vibrio adaptatus, Vibrio aerogenes, Vibrio aestivus, Vibrio aestuarianus, Vibrio agarivorans, Vibrio albensis, Vibrio alfacsensis, Vibrio alginolyticus, Vibrio anguillarum, Vibrio areninigrae, Vibrio artabrorum, Vibrio atlanticus, Vibrio atypicus, Vibrio azureus, Vibrio brasiliensis, Vibrio bubulus, Vibrio calviensis, Vibrio campbellii, Vibrio casei, Vibrio chagasii, Vibrio cholera, Vibrio cincinnatiensis, Vibrio coralliilyticus, Vibrio crassostreae, Vibrio cyclitrophicus, Vibrio diabolicus, Vibrio diazotrophicus, Vibrio ezurae, Vibrio fluvialis, Vibrio fortis, Vibrio furnissii, Vibrio gallicus, Vibrio gazogenes, Vibrio gigantis, Vibrio halioticoli, Vibrio harveyi, Vibrio hepatarius, Vibrio hippocampi, Vibrio hispanicus, Vibrio ichthyoenteri, Vibrio indicus, Vibrio kanaloae, Vibrio lentus, Vibrio litoralis, Vibrio logei, Vibrio mediterranei, Vibrio metschnikovii, Vibrio mimicus, Vibrio mytili, Vibrio natriegens, Vibrio navarrensis, Vibrio neonates, Vibrio neptunius, Vibrio nereis, Vibrio nigripulchritudo, Vibrio ordalii, Vibrio orientalis, Vibrio pacinii, Vibrio parahaemolyticus, Vibrio pectenicida, Vibrio penaeicida, Vibrio pomeroyi, Vibrio ponticus, Vibrio proteolyticus, Vibrio rotiferianus, Vibrio ruber, Vibrio rumoiensis, Vibrio salmonicida, Vibrio scophthalmi, Vibrio splendidus, Vibrio superstes, Vibrio tapetis, Vibrio tasmaniensis, Vibrio tubiashii, Vibrio vulnificus, Vibrio wodanis, and Vibrio xuii.

In some embodiments, the motile bacteria is Heliobacter pylori. The bacteria from the Selenomonas genus may include one or more of the following: Selenomonas acidaminovorans, Selenomonas artemidis, Selenomonas dianae, Selenomonas flueggei, Selenomonas infelix, Selenomonas lacticifex, Selenomonas lipolytica, Selenomonas noxia, Selenomonas palpitans, Selenomonas ruminantium, and Selenomonas sputigena.

Additionally, it is possible that the bacteria may include bacteria from different genera. In some embodiments, the active matter includes both living and non-living particles.

The motile bacteria may include at least one flagellum.

A flagellum is a relatively long, whip-like appendage that protrudes from the cell body of some prokaryotic and eukaryotic cells. Flagella enable locomotion. The flagella may be arranged in monotrichous, lophotrichous, amphitrichous, and/or peritrichous schemes. Monotrichous bacteria are bacteria having one flagellum. Lophotrichous bacteria include a plurality of flagella located at the same spot on the surface of the bacteria. Lophotrichous flagella may act in harmony to move the bacteria in a single direction. Amphitrichous bacteria include two flagella: one on each of two opposing ends. Peritrichous bacteria have flagella extending in many directions.

The active matter may also be motile cells that are not bacteria cells, such as sperm cells.

In some embodiments, the liquid crystal includes at least one of: disodium chromoglycate and Sunset Yellow dispersed in water.

The photoalignment layers 130, 135 may contain a photosensitive material, such as a dichroic dye (e.g., a dye that absorbs light anisotropically such as Brilliant Yellow or another azo dye). As used herein, the term "azo dye" refers to a dye containing an azo compound. In some embodiments, the azo compound has the general formula

wherein R and R' can be aryl or alkyl. The aryl or alkyl may be substituted.

As used herein, "Brilliant Yellow" refers to an azo dye having the following structure:

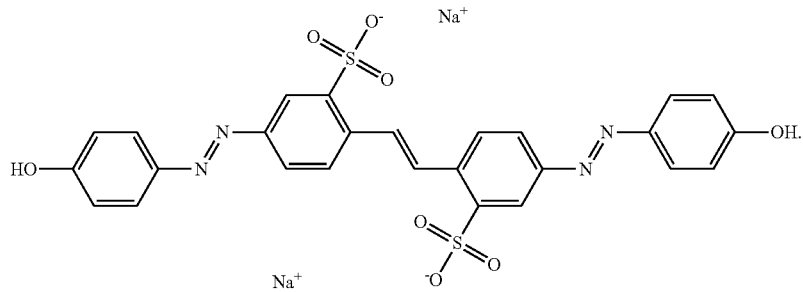

The alignment layers 120, 125 may contain a polymerizable liquid crystal material, such as a reactive mesogen (such as RM-257 or another polymer liquid crystal with polymerizable acrylic groups). In some embodiments, the polymer liquid crystal compound has the formula:

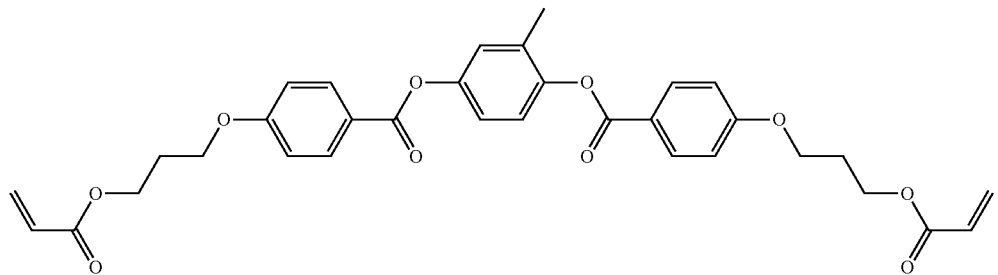

In some embodiments, the photoalignment layer is used to align the alignment layer (e.g., a Brilliant Yellow layer is used to align a RM-257 layer). The alignment of RM257 may occur because of anisotropic interactions between a material in the photoalignment layer (e.g., Brilliant Yellow) and a material in the alignment layer (e.g., RM-257). The material in the alignment layer (e.g., RM-257) can be polymerized, thereby fixing the memory of the orientation pattern in the material in the photoalignment layer (e.g., Brilliant Yellow). Then, the liquid crystal in the liquid crystal layer may recognize the orientation pattern in the alignment layer (e.g., RM-257 layer) and align accordingly. The alignment layer material may also serve as a barrier for water that is present in the liquid crystal but cannot penetrate through the alignment layer to dissolve the material in the photoalignment layer. Alignment layers 120, 125 may also be referred to a protective layers based at least in part on this barrier function.

The spatially-varied patterns of the present disclosure may be designed with well-defined deformations (e.g., pure bend, pure splay, or mixed splay-bend. The preimposed patterns command the self-propelled bacteria or other motile particles or biological organisms dispersed in the liquid crystal by controlling (i) geometry of trajectories, (ii) polarity of locomotion, and/or (iii) spatial distribution of bacteria or particles concentration. Bacteria may distinguish subtle differences in director deformations that occur over length scales much larger than their bodies. Bacteria swimming may be bipolar in pure-bend and pure-splay regions but unipolar in the mixed splay-bend case. The bacteria may tend to move closer to defects of a positive topological charge and avoid negative charges.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A method for controlling at least one of a local concentration, trajectory, or net flow of self-propelled particles, comprising:
   providing a liquid crystal cell, the liquid crystal cell comprising in sequence:
   a first plate;
   a first photoalignment layer;
   a first alignment layer;
   a liquid crystalline medium;
   a second alignment layer;
   a second photoalignment layer; and
   a second plate;
   generating a spatially-distorted pattern via irradiation of the first photoalignment layer and the second photoalignment layer;

polymerizing the first alignment layer and the second alignment layer and forming predesigned local ordering in the liquid crystalline medium; and providing the self-propelled particles to the liquid crystalline medium having predesigned local ordering.

2. The method of claim 1, wherein the self-propelled particles are living.

3. The method of claim 1, wherein the self-propelled particles are non-living.

4. The method of claim 1, wherein the self-propelled particles are motile microorganisms.

5. The method of claim 1, wherein the self-propelled particles are motile bacteria.

6. The method of claim 5, wherein the bacteria are of the genus *Bacillus*.

7. The method of claim 6, wherein the bacteria comprise at least one species selected from the group consisting of *Bacillus acidiceler, Bacillus acidicola, Bacillus acidiproducens, Bacillus acidocaldarius, Bacillus acidoterrestris, Bacillus aeolius, Bacillus aerius, Bacillus aerophilus, Bacillus agaradhaerens, Bacillus agri, Bacillus aidingensis, Bacillus akibai, Bacillus alcalophilus, Bacillus algicola, Bacillus alginolyticus, Bacillus alkalidiazotrophicus, Bacillus alkalinitrilicus, Bacillus alkalisediminis, Bacillus alkalitelluris, Bacillus altitudinis, Bacillus alveayuensis, Bacillus alvei, Bacillus amyloliquefaciens, Bacillus aminovorans, Bacillus amylolyticus, Bacillus andreesenii, Bacillus aneurinilyticus, Bacillus anthracis, Bacillus aquimaris, Bacillus arenosi, Bacillus arseniciselenatis, Bacillus arsenicus, Bacillus aurantiacus, Bacillus arvi, Bacillus aryabhattai, Bacillus asahii, Bacillus atrophaeus, Bacillus axarquiensis, Bacillus azotofixans, Bacillus azotoformans, Bacillus badius, Bacillus barbaricus, Bacillus bataviensis, Bacillus beijingensis, Bacillus benzoevorans, Bacillus beringensis, Bacillus berkeleyi, Bacillus beveridgei, Bacillus bogoriensis, Bacillus boroniphilus, Bacillus borstelensis, Bacillus brevis Migula, Bacillus butanolivorans, Bacillus canaveralius, Bacillus carboniphilus, Bacillus cecembensis, Bacillus cellulosilyticus, Bacillus centrosporus, Bacillus cereus, Bacillus chagannorensis, Bacillus chitinolyticus, Bacillus chondroitinus, Bacillus choshinensis, Bacillus chungangensis, Bacillus cibi, Bacillus circulans, Bacillus clarkia, Bacillus clausii, Bacillus coagulans, Bacillus coahuilensis, Bacillus cohnii, Bacillus composti, Bacillus curdlanolyticus, Bacillus cycloheptanicus, Bacillus cytotoxicus, Bacillus daliensis, Bacillus decisifrondis, Bacillus decolorationis, Bacillus deserti, Bacillus dipsosauri, Bacillus drentensis, Bacillus edaphicus, Bacillus ehimensis, Bacillus eiseniae, Bacillus enclensis, Bacillus endophyticus, Bacillus endoradicis, Bacillus farraginis, Bacillus fastidiosus, Bacillus fengqiuensis, Bacillus firmus, Bacillus flexus, Bacillus foraminis, Bacillus fordii, Bacillus formosus, Bacillus fortis, Bacillus fumarioli, Bacillus funiculus, Bacillus fusiformis, Bacillus galactophilus, Bacillus galactosidilyticus, Bacillus galliciensis, Bacillus gelatini, Bacillus gibsonii, Bacillus ginseng, Bacillus ginsengihumi, Bacillus ginsengisoli, Bacillus globisporus, Bacillus glucanolyticus, Bacillus gordonae, Bacillus gottheilii, Bacillus graminis, Bacillus halmapalus, Bacillus haloalkaliphilus, Bacillus halochares, Bacillus halodenitrificans, Bacillus halodurans, Bacillus halophilus, Bacillus halosaccharovorans, Bacillus hemicellulosilyticus, Bacillus hemicentroti, Bacillus herbersteinensis, Bacillus horikoshii, Bacillus horneckiae, Bacillus horti, Bacillus huizhouensis, Bacillus humi, Bacillus hwajinpoensis, Bacillus idriensis, Bacillus indicus, Bacillus infantis, Bacillus infernus, Bacillus insolitus, Bacillus invictae, Bacillus iranensis, Bacillus isabeliae, Bacillus isronensis, Bacillus jeotgali, Bacillus kaustophilus, Bacillus kobensis, Bacillus kochii, Bacillus kokeshiiformis, Bacillus koreensis, Bacillus korlensis, Bacillus kribbensis, Bacillus krulwichiae, Bacillus laevolacticus, Bacillus larvae, Bacillus laterosporus, Bacillus lautus, Bacillus lehensis, Bacillus lentimorbus, Bacillus lentus, Bacillus licheniformis, Bacillus ligniniphilus, Bacillus litoralis, Bacillus locisalis, Bacillus luciferensis, Bacillus luteolus, Bacillus luteus, Bacillus macauensis, Bacillus macerans, Bacillus macquariensis, Bacillus macyae, Bacillus malacitensis, Bacillus mannanilyticus, Bacillus marisflavi, Bacillus marismortui, Bacillus marmarensis, Bacillus massiliensis, Bacillus megaterium, Bacillus mesonae, Bacillus methanolicus, Bacillus methylotrophicus, Bacillus migulanus, Bacillus mirabilis, Bacillus mojavensis, Bacillus mucilaginosus, Bacillus muralis, Bacillus murimartini, Bacillus mycoides, Bacillus naganoensis, Bacillus nanhaiensis, Bacillus nanhaiisediminis, Bacillus nealsonii, Bacillus neidei, Bacillus neizhouensis, Bacillus niabensis, Bacillus niacin, Bacillus novalis, Bacillus oceanisediminis, Bacillus odyssey, Bacillus okhensis, Bacillus okuhidensis, Bacillus oleronius, Bacillus oryzaecorticis, Bacillus oshimensis, Bacillus pabuli, Bacillus pakistanensis, Bacillus pallidus, Bacillus pallidus, Bacillus panacisoli, Bacillus panaciterrae, Bacillus pantothenticus, Bacillus parabrevis, Bacillus paraflexus, Bacillus pasteurii, Bacillus patagoniensis, Bacillus peoriae, Bacillus persepolensis, Bacillus persicus, Bacillus pervagus, Bacillus plakortidis, Bacillus pocheonensis, Bacillus polygoni, Bacillus polymyxa, Bacillus popilliae, Bacillus pseudalcalophilus, Bacillus pseudofirmus, Bacillus pseudomycoides, Bacillus psychrodurans, Bacillus psychrophilus, Bacillus psychrosaccharolyticus, Bacillus psychrotolerans, Bacillus pulvifaciens, Bacillus pumilus, Bacillus purgationiresistens, Bacillus pycnus, Bacillus qingdaonensis, Bacillus qingshengii, Bacillus reuszeri, Bacillus rhizosphaerae, Bacillus rigui, Bacillus ruris, Bacillus safensis, Bacillus salaries, Bacillus salexigens, Bacillus saliphilus, Bacillus schlegelii, Bacillus sediminis, Bacillus selenatarsenatis, Bacillus selenitireducens, Bacillus seohaeanensis, Bacillus shacheensis, Bacillus shackletonii, Bacillus siamensis, Bacillus silvestris, Bacillus simplex, Bacillus spiralis, Bacillus smithii, Bacillus soli, Bacillus solimangrovi, Bacillus solisalsi, Bacillus songklensis, Bacillus sonorensis, Bacillus sphaericus, Bacillus sporothermodurans, Bacillus stearothermophilus, Bacillus stratosphericus, Bacillus subterraneus, Bacillus subtilis, Bacillus taeanensis, Bacillus tequilensis, Bacillus thermantarcticus, Bacillus thermoaerophilus, Bacillus thermoamylovorans, Bacillus thermocatenulatus, Bacillus thermocloacae, Bacillus thermocopriae, Bacillus thermodenitrificans, Bacillus thermoglucosidasius, Bacillus thermolactis, Bacillus thermoleovorans, Bacillus thermophiles, Bacillus thermoruber, Bacillus thermosphaericus, Bacillus thiaminolyticus, Bacillus thioparans, Bacillus thuringiensis, Bacillus tianshenii, Bacillus trypoxylicola, Bacillus tusciae, Bacillus validus, Bacillus vallismortis, Bacillus vedderi, Bacillus*

*velezensis, Bacillus vietnamensis, Bacillus vireti, Bacillus vulcani, Bacillus wakoensis, Bacillus weihenstephanensis, Bacillus xiamenensis, Bacillus xiaoxiensis, and Bacillus zhanjiangensis.*

8. The method of claim 1, wherein the liquid crystalline medium comprises a lyotropic chromonic liquid crystal confined between two plates.

9. The method of claim 8, wherein the plates are coated with a layer of a surface aligning agent that imposes a certain alignment direction of the adjacent liquid crystal, this layer can comprise photosensitive molecules.

10. The method of claim 9, further comprising:
    irradiating the photosensitive molecules with a light beam of linear polariziation that changes from point to point to thereby align the photosensitive molecules with local polarization; and
    photopolymerizing the alignment layer with unpolarized UV light;
    wherein the surface molecules align a director of liquid crystals in the liquid crystalline medium.

11. The method of claim 1, wherein the liquid crystalline medium comprises a liquid crystalline layer having a thickness of from about 3 μm to about 7 μm.

12. The method of claim 11, wherein the thickness is from about 4.5 μm to about 5.5 μm.

13. The method of claim 1, wherein the predesigned local ordering includes splay-bend regions; and wherein the self-propelled particles swim unipolarly in the liquid crystalline medium due to the predesigned local ordering.

14. The method of claim 1, wherein the predesigned local ordering includes arrays of periodically or non-periodically distorted director to control concentration (spatial distribution), trajectories, and polarity of propulsion of motile particles.

15. The method of claim 1, wherein the predesigned local ordering includes arrays of periodically or non-periodically placed topological defects of various strength or topological charge to control concentration (spatial distribution), trajectories, and polarity of propulsion of motile particles.

16. The method of claim 1, wherein the predesigned local ordering includes pairs of semi-integer-strength or integer-strength defects to create a pumping action.

17. The method of claim 1, wherein the liquid crystalline medium comprises disodium chromoglycate dissolved in water.

18. The method of claim 1, wherein the first photoalignment layer and the second photoalignment layer comprise an azo dye of the formula:

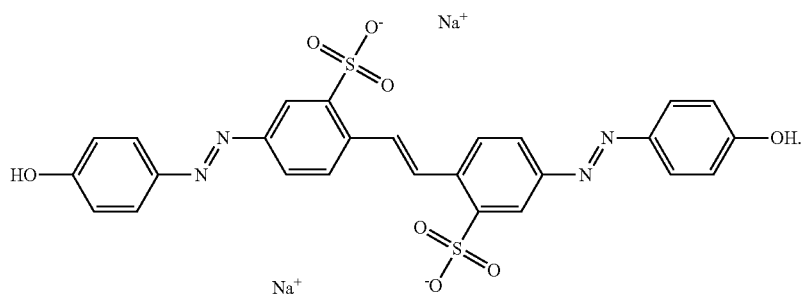

19. The method of claim 1, wherein the first alignment layer and the second alignment layer comprise a polymerizable liquid crystal material of the following formula:

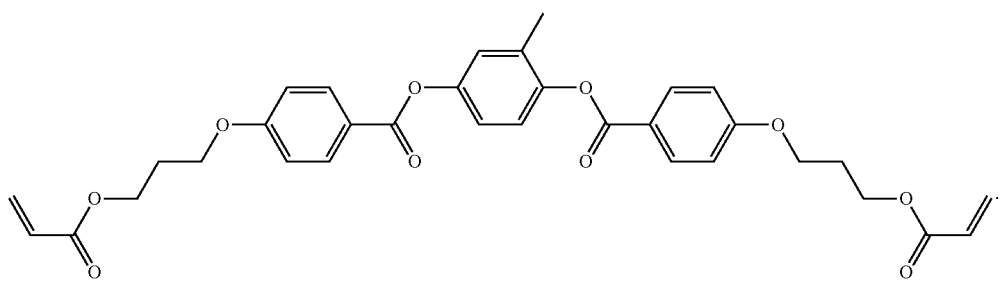 [SMILES: C=CC(=O)OCCCOc1ccc(C(=O)Oc2ccc(OC(=O)c3ccc(OCCCOC(=O)C=C)cc3)c(C)c2)cc1]

20. The method of claim 1, wherein the first photoalignment layer and the second photoalignment layer comprise an azo dye of the formula:
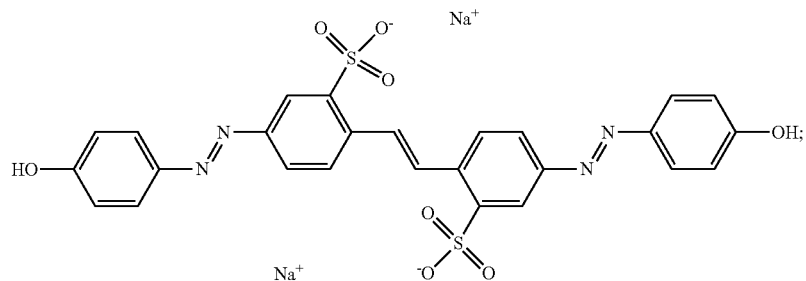
and
wherein the first alignment layer and the second alignment layer comprise a polymerizable liquid crystal material of the following formula:
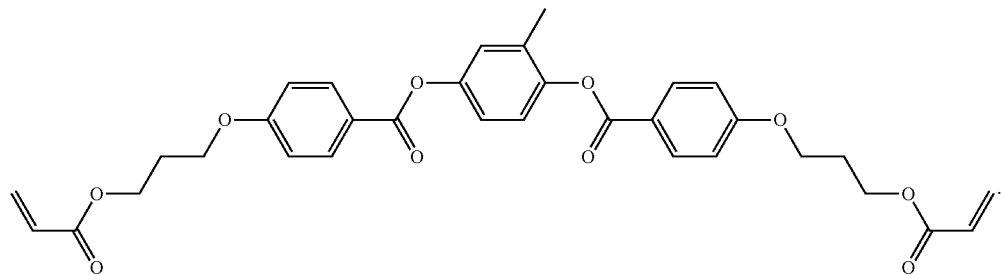 [SMILES: C=CC(=O)OCCCOc1ccc(C(=O)Oc2ccc(OC(=O)c3ccc(OCCCOC(=O)C=C)cc3)c(C)c2)cc1]
* * * * *